US006846178B2

(12) United States Patent
Freeman, Jr. et al.

(10) Patent No.: US 6,846,178 B2
(45) Date of Patent: Jan. 25, 2005

(54) ORTHODONTIC BRACKET BASE APPARATUS AND METHOD OF MANUFACTURE

(75) Inventors: Ray Winston Freeman, Jr., Pine, CO (US); George Kantor, Denver, CO (US); Rosilio Ronald Perez, Littleton, CO (US); Paul Ritter Smith, Denver, CO (US); Michael Dean Stevens, Littleton, CO (US); Daphne Upchurch, Lakewood, CO (US)

(73) Assignee: RMO, Inc., Denver, CO (US)

( * ) Notice: Subject to any disclaimer, the term of this patent is extended or adjusted under 35 U.S.C. 154(b) by 66 days.

(21) Appl. No.: 10/284,016

(22) Filed: Oct. 29, 2002

(65) Prior Publication Data

US 2004/0081936 A1 Apr. 29, 2004

(51) Int. Cl.[7] .............................................. A61C 3/00
(52) U.S. Cl. ......................................................... 433/9
(58) Field of Search ........................ 433/8, 9; D24/180

(56) References Cited

U.S. PATENT DOCUMENTS

| | | | |
|---|---|---|---|
| 4,430,061 A | 2/1984 | Webb et al. ................... 433/9 |
| 4,626,209 A | 12/1986 | Tsai et al. ...................... 433/9 |
| 4,659,309 A | 4/1987 | Merkel .......................... 433/9 |
| 4,661,059 A | 4/1987 | Kanno ........................... 433/9 |
| D290,040 S | 5/1987 | Kelly .......................... D24/16 |
| D291,919 S | 9/1987 | Reynolds ..................... D24/10 |
| 4,752,221 A | 6/1988 | Hanson et al. ................. 433/9 |
| 4,819,316 A | 4/1989 | Rossini et al. ............. 29/160.6 |
| 4,838,786 A | 6/1989 | Reher et al. .................... 433/9 |
| 5,022,854 A | 6/1991 | Broughton et al. ............ 433/8 |
| 5,044,945 A | 9/1991 | Peterson ....................... 433/8 |
| 5,066,225 A | 11/1991 | Forbes Jones et al. .......... 433/8 |
| D322,482 S | 12/1991 | Ianieri et al. .............. D24/180 |
| 5,095,602 A | 3/1992 | Reher et al. ................ 29/160.6 |
| 5,125,831 A | 6/1992 | Pospisil .......................... 433/8 |
| 5,160,261 A | 11/1992 | Peterson ........................ 433/8 |
| D331,975 S | 12/1992 | Pospisil ..................... D24/180 |
| D340,523 S | 10/1993 | Barngrover ................ D24/180 |
| 5,267,855 A | 12/1993 | Tuneberg ........................ 433/9 |
| 5,269,680 A | 12/1993 | Kawaguchi ..................... 433/9 |
| 5,441,409 A * | 8/1995 | Tuneberg ...................... 433/23 |
| 5,470,228 A | 11/1995 | Franseen et al. ............... 433/8 |
| 5,522,725 A | 6/1996 | Jordan et al. ................... 433/9 |
| 5,595,484 A | 1/1997 | Orikasa et al. ................. 433/8 |
| 5,597,302 A | 1/1997 | Pospisil et al. ................. 433/8 |
| 5,607,301 A | 3/1997 | Roman .......................... 433/8 |
| 5,618,175 A | 4/1997 | Reher et al. .................... 433/8 |
| 5,622,494 A | 4/1997 | Andreiko et al. ............... 433/9 |
| 5,692,898 A | 12/1997 | Orikasa et al. ................. 433/8 |
| 5,746,592 A | 5/1998 | Nezu et al. ..................... 433/8 |
| 5,746,594 A | 5/1998 | Jordan et al. ................... 433/9 |
| RE35,863 E | 7/1998 | Sachdeva et al. ............... 433/8 |
| 5,829,972 A | 11/1998 | Frazin-Nia .................... 433/9 |
| 6,053,729 A | 4/2000 | Brehm et al. ................... 433/9 |
| 6,190,165 B1 | 2/2001 | Andreiko et al. ............... 433/9 |
| 6,227,849 B1 | 5/2001 | Brehm et al. ................... 433/9 |
| 6,394,798 B1 * | 5/2002 | Huff et al. ...................... 433/8 |

FOREIGN PATENT DOCUMENTS

JP 11276504 * 10/1999

* cited by examiner

Primary Examiner—Cary E. O'Connor
(74) Attorney, Agent, or Firm—Sheridan Ross P.C.

(57) ABSTRACT

The present invention comprises a continuous series of alpha-numeric characters (such as letters or numerals) or symbols (such as company logos) that are formed in a manner such that the symbols or characters on the base of the bracket serve as texturing to facilitate bonding of the bracket with the tooth when the base of the bracket is attached to the tooth using an adhesive. In a separate aspect of the invention, a perimeter rail, and more preferably, a discontinuous perimeter rail may be used at the edge of the base. A method for forming a bracket is also provided.

91 Claims, 7 Drawing Sheets

FIG. 11 the space between and around the characters is recessed, and the characters themselves are projected.

In a separate aspect of the invention, a perimeter rail, and more preferably, a discontinuous perimeter rail may be used at the edge of the base. The discontinuous perimeter rail, if used, is in contact with the tooth surface, with the interior portion of the base pattern recessed relative to the surface of the discontinuous perimeter rail. If used, the perimeter rail forms a pocket to the interior of the perimeter rail that receives the adhesive. Thus, if used, a perimeter rail contacts the tooth surface, with the base pattern recessed relative to the surface of the perimeter rail.

ORTHODONTIC BRACKET BASE APPARATUS AND METHOD OF MANUFACTURE

FIELD OF THE INVENTION

The present invention pertains to orthodontic brackets, and more particularly, to the base of orthodontic brackets.

BACKGROUND OF THE INVENTION

Texturing of the lingual surface of orthodontic brackets has been used to provide improved bonding between the bracket and the tooth to which the bracket is applied. For example, U.S. Pat. No. 5,522,725 concerns a method of improving the bond strength of a plastic bracket by temporarily heating and then permanently deforming projections located on the base of the bracket. The deformed projections interlock with adhesive when the bracket is bonded to a tooth. U.S. Pat. No. 5,595,484 discloses a plastic bracket having a metal reinforcement member partly embedded in the bracket body. FIG. 13 of the '484 patent discloses a bracket base having eight recessed discontinuous portions 36 that include molded identification characters 35. U.S. Pat. No. 5,622,494 discloses several structures, including a spiral-like ridge, concentric rectangles, and a weave pattern. Upon being deformed, each structure creates an undercut structure for forming a mechanical bond with an adhesive. However, this patent and the other patents noted above fail to disclose a base structure that includes lettering, symbols, or numerals that are substantially continuous and that functionally serve as texturing to bond the bracket to a patient's tooth. The present invention, amongst other things as described below, addresses these shortcomings.

SUMMARY OF THE INVENTION

The present invention concerns the base of orthodontic brackets. More particularly, the present invention concerns the use of texturing in the form of characters or symbols along the lingual surface at the base of the bracket that function to provide a texturing that serves to bond the bracket to a tooth when an adhesive is used to attach the bracket to a patient's tooth. Such features also serve identification and/or information purposes that are absent in all prior art devices.

The present invention comprises a substantially continuous series of alpha-numeric characters (such as letters or numerals) or symbols (such as company logos) that are formed in a manner such that the symbols or characters on the base of the bracket serve as texturing to facilitate bonding of the bracket with the tooth when the base of the bracket is attached to the tooth using an adhesive. Hereafter, the term "characters" refers to either letters, and/or numbers, and/or graphics, and/or symbols (such as logos), and/or a combination thereof. "Substantially continuous" is meant to convey the regular matrix-like aspect of the alpha-numeric characters configured on the base so as to facilitate a more or less uniform textured surface for bonding purposes.

The characters are preferably recessed, with the space between and around the characters projected. Thus, the projected space between the characters is either in contact with the tooth, or is the next surface closest to the tooth's surface if a perimeter rail is present, as discussed below. The surface of the recessed characters is preferably further away from the tooth surface than the space between the characters. Alternatively, the opposite arrangement may be used, where

BRIEF DESCRIPTION OF THE DRAWINGS

The figures are not necessarily to scale in order to visualize the various surfaces and relief associated with the bracket and its base structure.

DETAILED DESCRIPTION OF THE INVENTION

The present invention is a base structure for an orthodontic bracket. The base structure is applicable to any type of orthodontic bracket. More particularly, the base structure applies to brackets for any tooth, and can be used on brackets made of any material, such as plastic, metal, ceramics, or combinations thereof. Furthermore, the base structure is applicable to brackets formed as one unit, or brackets formed of a plurality of pieces that are assembled to form the bracket. For example, in one preferred embodiment, the base structure may be formed on the base of an injection molded metal bracket. Alternatively, it may be formed as an applique that is later applied to the underside of the body of the bracket, which is then installed on a tooth. In the latter case, the applique is either used to form the interconnection between the patient's tooth surface and the bracket itself, or it is the next closest surface to the tooth if a perimeter rail is present.

Figure 1:
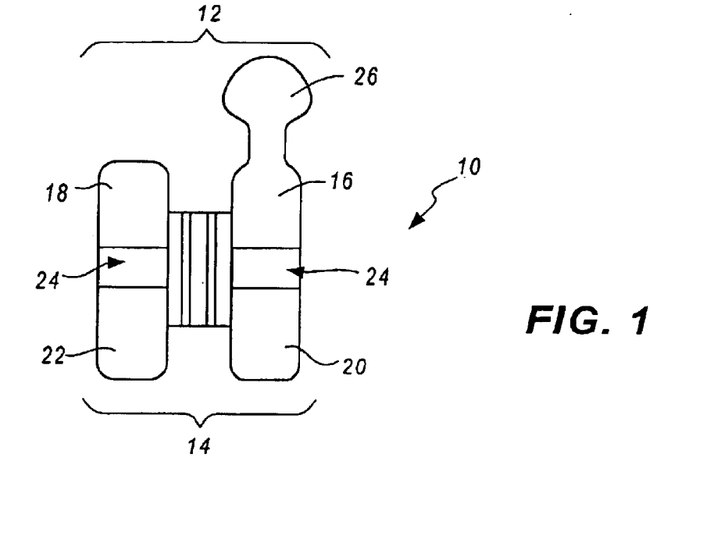
FIG. 1 is a front elevation view of a one-piece bracket that includes the present invention.

Referring now to FIGS. 1–5, a one-piece bracket with the base structure of the present invention is shown, wherein the base structure is formed as an integral part of the bracket itself during manufacture of the bracket. Accordingly, in one preferred embodiment, a bracket utilizes a one-piece metal injection molded construction, wherein the bracket includes a base structure having characters. FIG. 1 illustrates a view of the buccal side or front of an orthodontic twin bracket 10. The bracket 10 includes a gingival tie wing 12 and an occlusal tie wing 14. The gingival tie wing 12 includes a mesial wing tip 16 and a distal wing tip 18. The occlusal tie wing 14 includes a mesial wing tip 20 and a distal wing tip 22. Located between the gingival tie wing 12 and the occlusal tie wing 14 is a mesiodistal-extending archwire slot 24.

Extending from wing tip 16 is an optional attachment knob or hook 26. Typically, the hook 26 is on the gingival side of the bracket 10. The hook 26 can be used in conjunction with springs, ligation doughnuts, elastic ribbons, etc. to perform various tasks such as pulling another tooth into place, connecting the maxillary with the mandibular using elastics, etc. Preferably the hook 26 is located on the gingival side of brackets designed for cuspids and bicuspids.

Figure 2:
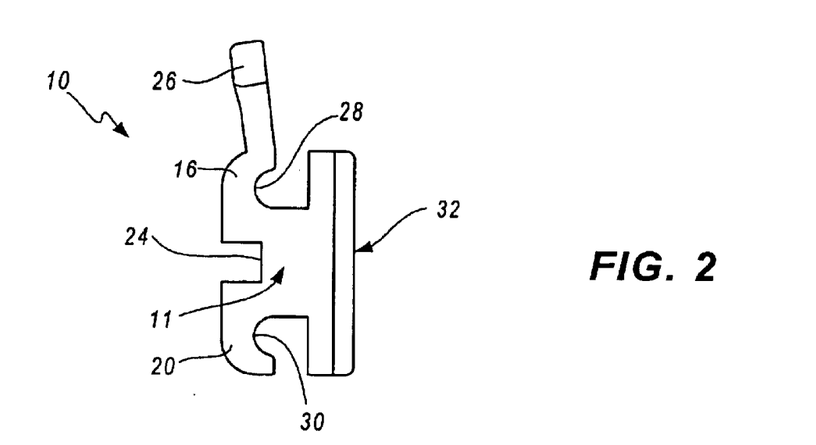
FIG. 2 is a side elevation view of the bracket shown in FIG. 1.

FIG. 2 is a mesial or front-side view of the bracket 10. Mesial wing tips 16,20 with the corresponding mesial ligature undercuts 28,30 are clearly illustrated. FIG. 2 also illustrates the two basic structures of the bracket 10, that is, body 11 and base 32. For the one-piece bracket embodiment, body 11 is integrally formed together with base 32 during manufacture of the bracket 10. In an alternate embodiment, body 11 may be formed separately from base 32, and base 32 may be subsequently connected to body 11, either before attachment to a tooth, or during attachment to a tooth.

Figure 3:
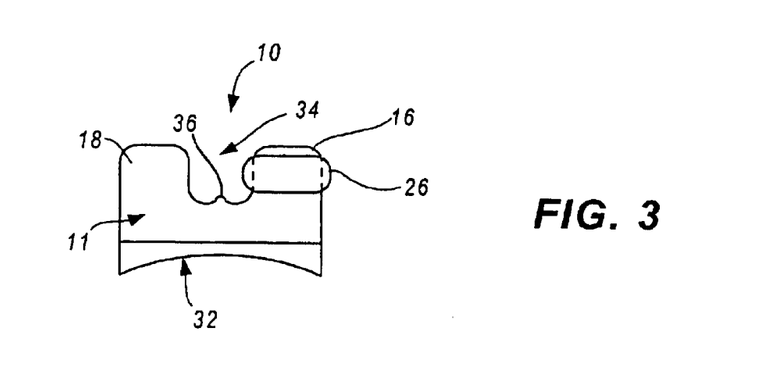
FIG. 3 is a top elevation view of the bracket shown in FIG. 1.

FIG. 3 shows bracket 10 from the gingival or top side. The base 32 of the bracket 10 and the open area or saddle 34 between the mesial wing tips 16,20 and the distal wing tips 18,22 are clearly illustrated. The saddle 34 permits the use of ligatures to hold down the archwire to be applied in various configurations. For example, the ligature can pass under the two mesial wing tips 16,20, under the two distal wing tips 18,22, or under all four wing tips 16,18,20,22. This allows the orthodontist to induce rotation by placing more pressure on one end of the bracket or another, or applying pressure evenly. Preferably, the saddle 34 includes a central saddle ridge 36. The saddle ridge 36 can provide a number of advantages. For example, it maintains the ligature in a desired location, it can help support the ligature above the top surface of the archwire, thus reducing friction, and it can improve the structural integrity of the bracket 10. Another advantage of the saddle 34 and the saddle ridge 36 is that they provide a convenient sight line or centering mark, to assist in the placement of the bracket 10 relative to the long axis of the tooth.

As shown in FIG. 3, the base 32 extends in a reference plane (or "plane of contour") that has a concave configuration adapted to match the convex, compound contour of the tooth for which the bracket 10 is intended. The reference plane or "plane of contour" may be curved, relatively flat, or essentially flat. Bracket base 32 can be customized for left or right tooth anatomy and to smoothly follow the facial and labial/buccal surface of the tooth.

Figure 4:
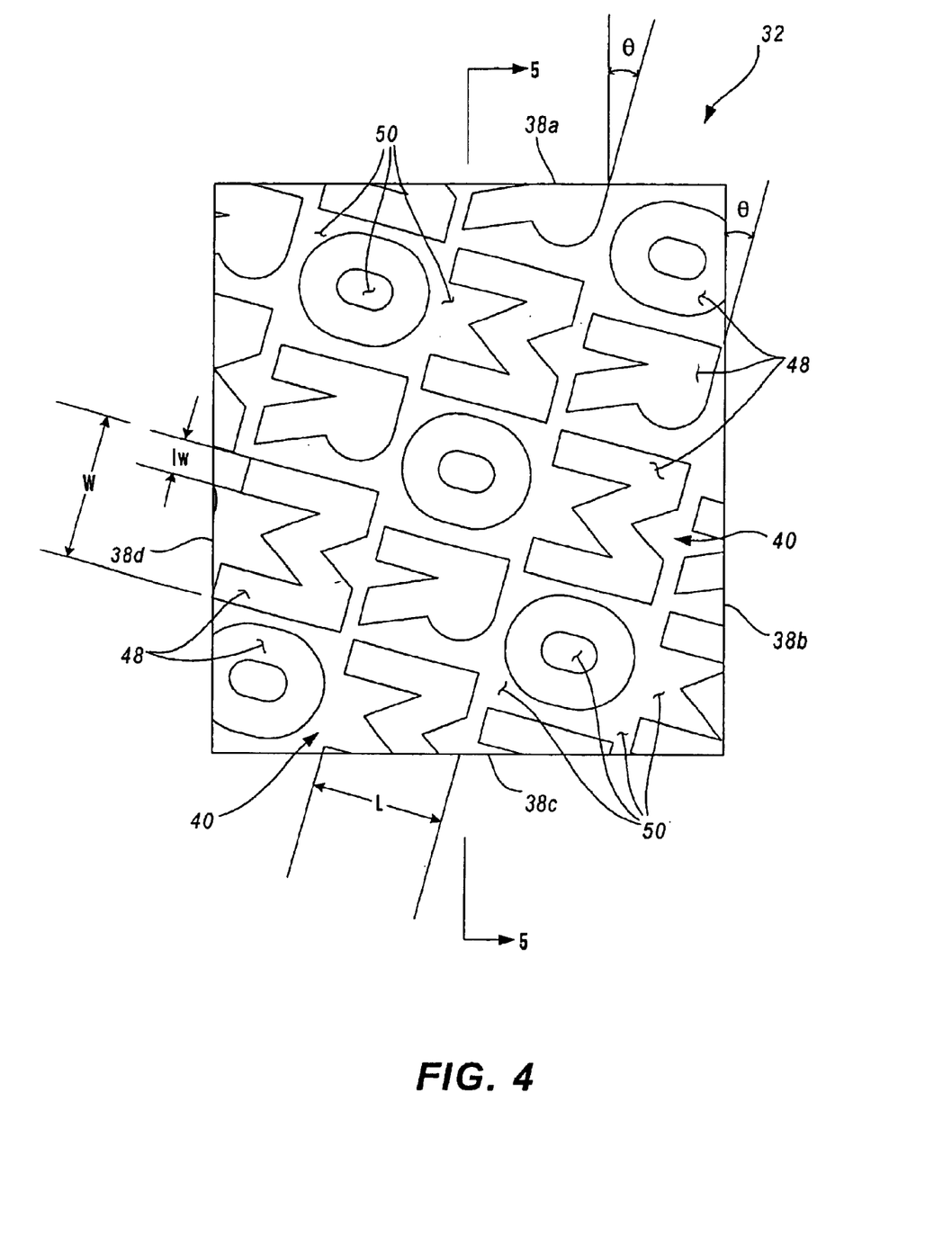
FIG. 4 is a rear elevation view of an example of the base structure that comprises the present invention.
Figure 5A:
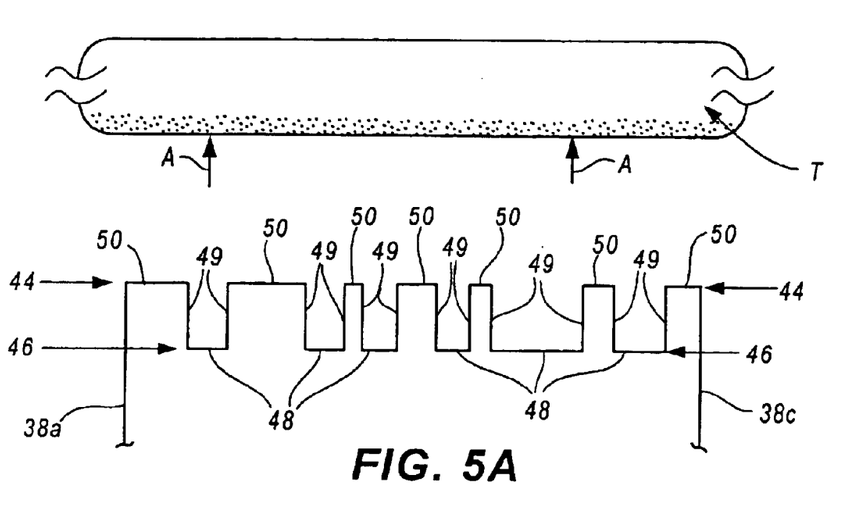
FIG. 5a is a cross-sectional view of FIG. 4 taken along line 5—5 with the characters recessed relative to the intermediate space.
Figure 5B:
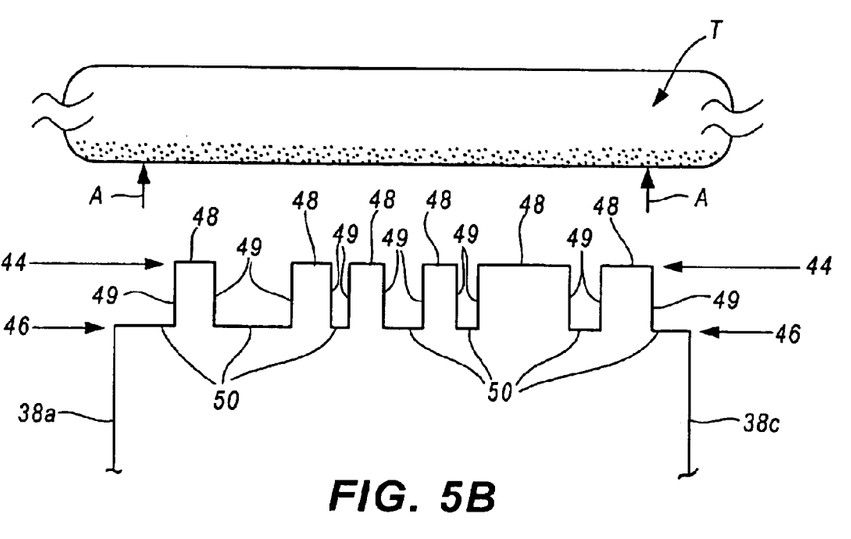
FIG. 5b is a second cross-sectional view of FIG. 4 taken along line 5—5 with the intermediate space recessed relative to the characters.

Referring now to FIG. 4, another aspect of the present invention is shown. FIG. 4 depicts an enlarged rear elevation view of the rear surface or base 32 of bracket 10. Base 32 includes gingival edge 38a, distal edge 38b, occlusal edge 38c, and mesial edge 38d. Within the interior of edges 38a,38b,38c, and 38d is interior region 40. Interior region 40 includes a projected surface 44 and a recessed surface 46, as depicted in FIGS. 5a and 5b. The projected surface 44 of the interior region 40 is a surface that is both essentially parallel to the tooth's surface and closest to the tooth's surface upon attachment of the bracket 10 to the tooth. The recessed surface 46 is a surface of the interior region 40 that is also parallel to the tooth's surface, but is further away from the tooth's surface than the projected surface 44 upon attachment of the bracket 10 to the tooth. The recessed surface 46 is preferably recessed between about 0.009 to 0.011 inches relative to the projected surface 44, and more preferably, the recessed surface is recessed about 0.010 inches relative to the projected surface 44.

Characters 48 and intermediate space 50 extend substantially continuously within interior region 40, between edges 38a,38b,38c, and 38d. The pattern of characters may be repeating, such as the letters "RMO"® shown in FIG. 4, or they may be a non-repeating series of characters 48. Alternately, the characters may be a set of information regarding the bracket 10, such as its intended installation location, manufacturer, date of manufacturer, model number, etc. As one of skill in the art will appreciate, the provision of particular useful information on the base, and having such encoded information perform a useful function with respect to the use of the device, is itself a novel and nonobvious characteristic of the present invention. Regardless of the nature of the characters 48 actually used, in a preferred embodiment, the base 32 does not have a grid between the characters 48. That is, in contrast to the bracket base shown in FIG. 13 of U.S. Pat. No. 5,595,484, the base 32 of the present invention does not have a grid or lattice within which the characters reside. Rather, the present invention uses characters 48 and a relatively irregular, non-grid like intermediate space 50 to cover the entire interior region 40. The characters 48 and intermediate space 50 thus function directly as the texturing that works in combination with the adhesive to bond the bracket to the tooth.

In a separate aspect of the present invention, the characters 48 may be angled at any orientation relative to the edges 38a,38b,38c, and 38d. More specifically, the characters may be oriented parallel with edges 38a and 38c, or perpendicular to edges 38a and 38c. Likewise, the characters may be oriented parallel with edges 38b and 38d, or perpendicular to edges 38b and 38d. Alternately, the characters 48 maybe oriented at an angle relative to edges 38a,38b,38c, and 38d. As an example without limitation, FIG. 4 illustrates that the characters 48 are oriented at an angle θ of about 15 degrees relative to edges 38b and 38d, and at an angle of about 75 degrees relative to edges 38a and 38c.

Character length "L" and width "W" may vary considerably. Referring now to FIG. 4, in a preferred embodiment, in plan view the length L of each character 48 is about 0.034 to 0.038 inches, and more preferably, about 0.036 inches. The width W of each character 48 varies with the length and with the specific character type. For example, in the character string "RMO"® shown in FIG. 4, an "M" is typically wider than an "R" or an "O".

For each character 48, the line width "lw" preferably ranges between about 0.008 to 0.010 inches, where line width lw is the width of the line forming each individual character 48. Typically, line width lw will vary with character length L. Therefore, shorter characters 48 will typically have thinner line widths lw. Obviously, logos, symbols and graphics will have lengths L, widths W, and line widths lw as required to form each individual type of shape.

The total surface area in rear elevation view, or the exterior surface of the base 32 is defined herein as the area in rear elevation view between edges 38a,38b,38c, and 38d for the base surfaces parallel to the tooth's surface. Whether the characters 48 are letters, numbers, logos, symbols, or graphics, preferably the recessed surface 46 comprises between about 50% to 60% of the total surface area of the base 32, and more preferably, about 55% of the total surface area of base 32. Correspondingly, preferably the projected surface 44 comprises between about 40% to 50% of the total surface area of the base 32, and more preferably, about 45% of the total surface area of the base 32.

Projected surface 44 and recessed surface 46 are comprised of characters 48 and intermediate space 50, which is situated between and around characters 48. Characters 48 may occupy the projected surface 44 of the base 32, but preferably occupy the recessed surface 46 of the base 32. Alternatively, intermediate space 50 may occupy the recessed surface 46 of base 32, but preferably occupy the projected surface 44 of base 32. Thus, in a preferred embodiment, upon attachment of the bracket 10 to the surface of a patient's tooth, intermediate space 50 is the projected surface 44 that is closer to the tooth surface than the characters 48 that are situated along the recessed surface 46. Separation between the characters 48 and intermediate space 50 is formed by bracket character walls 49 that are generally perpendicular or steeply sloped surfaces disposed between the characters 48 and the intermediate space 50. As shown in FIG. 5a, the projected surface 44 contacts the tooth surface upon attachment of the bracket 10 in the direction of arrows A to the patient's tooth T. Thus, as shown in FIG. 5a, when the intermediate space 50 occupies the projected surface 44, the intermediate surface 50 is closest to the tooth surface, and the location of characters 48 is recessed relative to the location of intermediate space 50. In contrast, FIG. 5b presents the same cross-sectional view of base 32 as that shown in FIG. 5a, but with the characters 48 and intermediate space 50 inverted. That is, in this modified arrangement, the location of intermediate space 50 is recessed relative to the location of the characters 48. Therefore, the characters 48 contact the tooth surface upon attachment of the bracket 10 in the direction of arrows A to the patient's tooth T.

Figure 6:
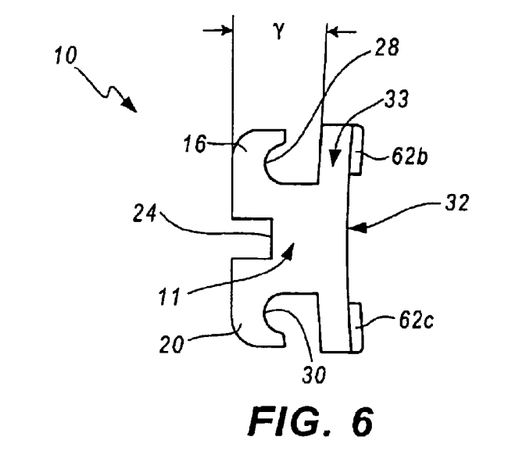
FIG. 6 is a side elevation view of a bracket that is a second embodiment of the present invention and that includes a discontinuous perimeter rail.
Figure 7:
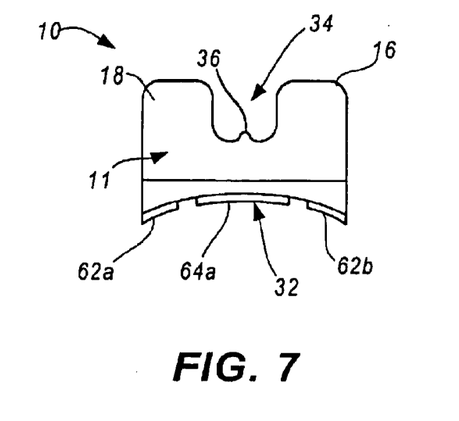
FIG. 7 is a top elevation view of the bracket shown in FIG. 6.

Referring now to FIG. 6, in yet a separate aspect of the invention, the bracket 10 may include a canted back portion 33. FIG. 6 shows a side elevation view of a bracket 10 having a canted back portion 33 that is sloped at an angle γ. As shown in FIG. 6, γ is approximately 5.4 degrees, however, back portion 33 may be set at a variety of angles depending upon the curvature of the patient's tooth surface.

Referring now to FIGS. 6–9, in yet a separate aspect of the invention, base 32 preferably includes a perimeter rail, and more preferably, a discontinuous perimeter rail.

Figure 8:
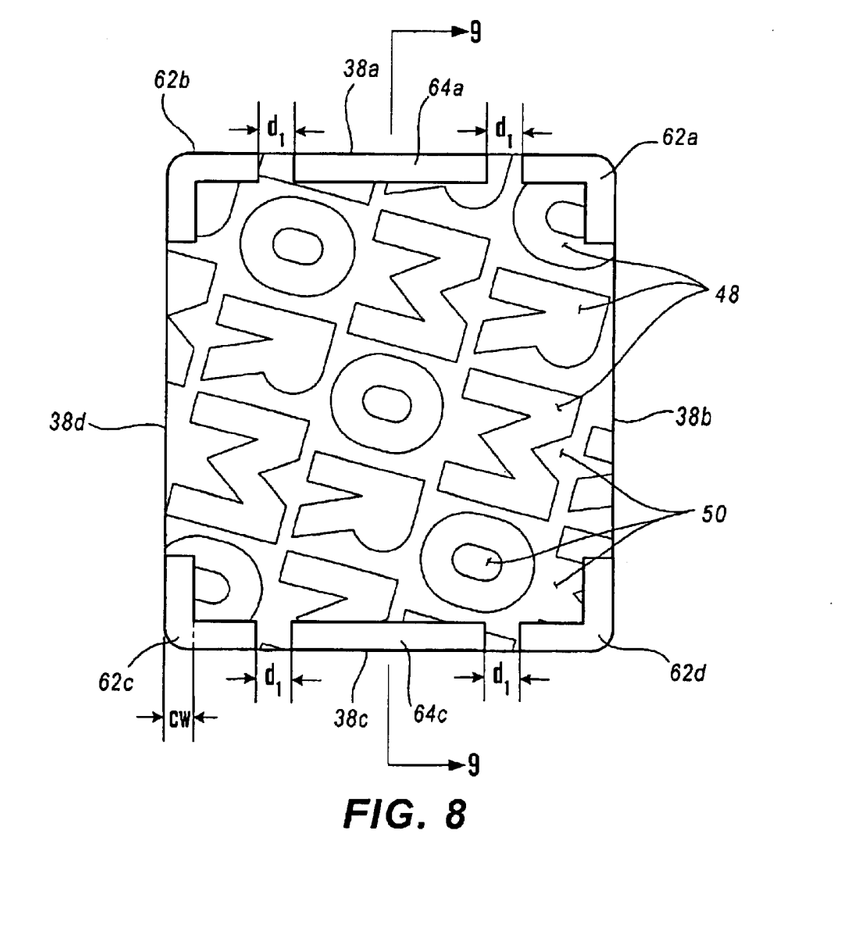
FIG. 8 is a rear elevation view of an example of the base structure of the present invention that is associated with the bracket depicted in FIG. 6.

The discontinuous perimeter rail preferably includes at least one corner segment, and more preferably, a plurality of corner segments, including a distal/gingival corner 62a, a gingival/mesial corner 62b, a mesial/occlusal corner 62c, and an occlusal/distal corner 62d.

Corners 62a,62b,62c, and 62d are preferably between about 0.008 to 0.011 inches in width "cw", and more preferably, are about 0.085 inches wide. Each corner 62a, 62b,62c, and 62d is separated from the other corners segments by a distance or a cavity. Preferably, the discontinuous perimeter rail also includes at least one straight segment, and more preferably, a plurality of straight segments. More preferably yet, two straight segments are provided, namely a gingival straight segment 64a and an occlusal straight segment 64c. The gingival straight segment 64a is separated from the distal/gingival corner 62a and the gingival/mesial corner 62b by a cavity or a distance "$d_1$" of about 0.008 to 0.011 inches, and more preferably, by a distance $d_1$ approximately equal to the width of the discontinuous perimeter rail, or about 0.0085 inches. Similarly, the occlusal straight segment 64c is separated from the mesial/occlusal corner 62c and the occlusal/distal corner 62d by a cavity or distance $d_1$ of about 0.008 to 0.011 inches, and more preferably, by a distance $d_1$ approximately equal to the width of the discontinuous perimeter rail, or about 0.0085 inches. Although base 32 will function without a perimeter rail, the discontinuous perimeter rail in combination with characters 48 increases the bonding strength of bracket 10 when it is attached to a tooth using an adhesive.

Referring now to FIG. 8, although it may be present, in a preferred embodiment, the discontinuous perimeter rail does not include a distal straight segment between the distal/gingival corner 62a and the occlusal/distal corner 62d. In addition, in a preferred embodiment, the discontinuous perimeter rail does not include a mesial straight segment between the gingival/mesial corner 62b and the mesial/occlusal corner 62c.

Still referring to FIG. 8, in a preferred embodiment, the perimeter rail is preferably positioned within the base area defined by edges 38a,38b,38c, and 38d. More specifically, corners 62a,62b,62c, and 62d, as well as straight segments 64a and 64c of the discontinuous perimeter rail are all disposed within the interior of the area defined by base edges 38a,38b,38c, and 38d. The total surface area in rear elevation view, or the exterior surface of the base 32 is defined herein as the area in rear elevation view between edges 38a,38b,38c, and 38d for the base surfaces parallel to the tooth's surface. Where a discontinuous perimeter rail is used, the discontinuous perimeter rail portions 62a,62b,62c, 62d,64a and 64c comprise between about 12% to 16% of the total surface area of the base 32, and more preferably, about 14% of the total surface area of base 32. Whether the characters 48 are letters, numbers, logos, symbols, or graphics, when a discontinuous perimeter rail is present, preferably the recessed surface 46 comprises between about 45% to 50% of the total surface area of the base 32, and more preferably, about 48% of the total surface area of base 32. Correspondingly, when a discontinuous perimeter rail is present, preferably the projected surface 44 comprises between about 35% to 40% of the total surface area of the base 32, and more preferably, about 38% of the total surface area of the base 32.

Figure 9A:
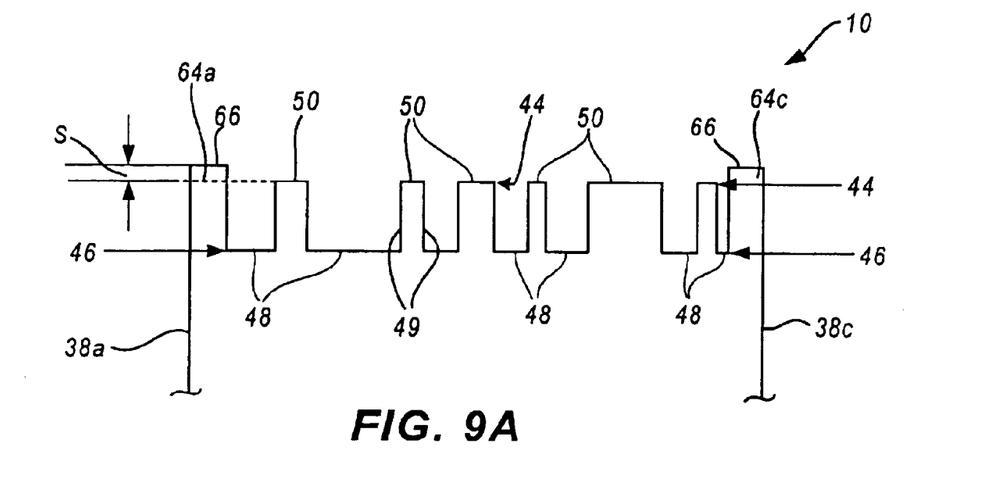
FIG. 9 is a cross-sectional view of FIG. 8 taken along line 9—9 with the characters recessed relative to the intermediate space.
Figure 9B:
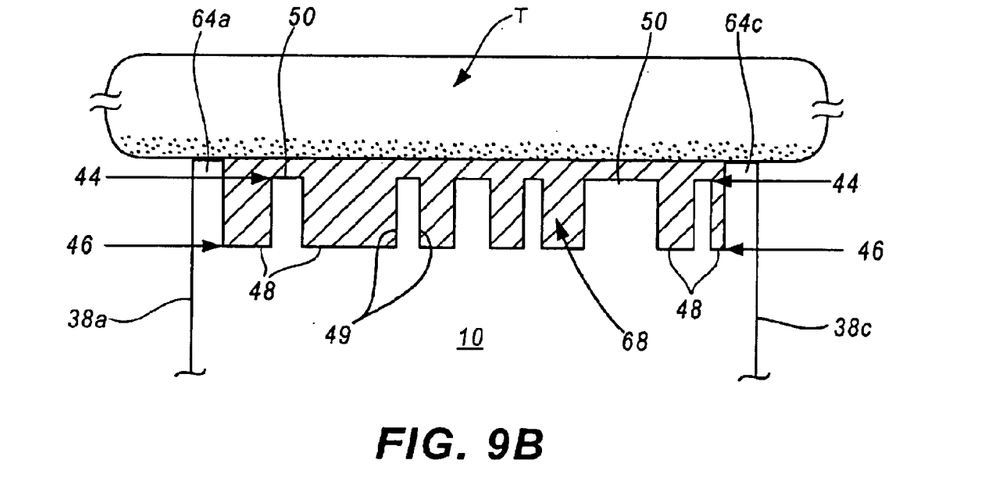

Referring now to FIG. 9a, a cross-sectional view along line 9—9 as shown in FIG. 8 is provided. The cross-sectional view of FIG. 9a shows the gingival straight segment 64a and the occlusal straight segment 64c along the gingival and occlusal edges of the bracket 10. FIG. 9a also shows that the rail surface 66 is disposed beyond the projected surface 44. In the preferred embodiment depicted in FIG. 9a, the projected surface 44 is comprised of the intermediate space 50 between characters 48, while the recessed surface 46 is comprised of the characters 48. The rail surface 66 preferably projects a distance "s" of about 0.002 to 0.004 inches beyond the projected surface 44, and more preferably, the rail surface 66 projects about 0.003 inches beyond the projected surface 44. Thus, when bracket 10 having a discontinuous rail is placed with its base 32 in contact with a patient's tooth, the rail surface 66 contacts the patient's tooth. The discontinuous rail thus forms a pocket for the collection of adhesive. Upon application of the bracket 10 to a patient's tooth, the openings between the perimeter rail permit excess adhesive to escape under the applied pressure, thereby preventing the bracket 10 from having an adhesive layer that is too thick and moving away from the tooth as a result of increased hydraulic pressure formed within the adhesive pocket when the bracket is first pressed against the tooth to which it is being applied. Thus, the discontinuous structure of the perimeter rail improves the bonding strength between the bracket and the patient's tooth because it allows excess adhesive to escape during the application of the bracket 10 to the tooth's surface. Furthermore, as shown in FIG. 9b, the difference in distance provided by the projection of the perimeter rail beyond the projected surface 44 allows a layer of adhesive 68 to bond between the projected surface 44 and the tooth's surface. Thus, a layer of adhesive is formed within the entire interior area 40 of the base that is not otherwise occupied by the discontinuous perimeter rail segments 62a–d, and 64a and 64c. This further improves bonding between the bracket 10 and the tooth's surface.

Figure 10:
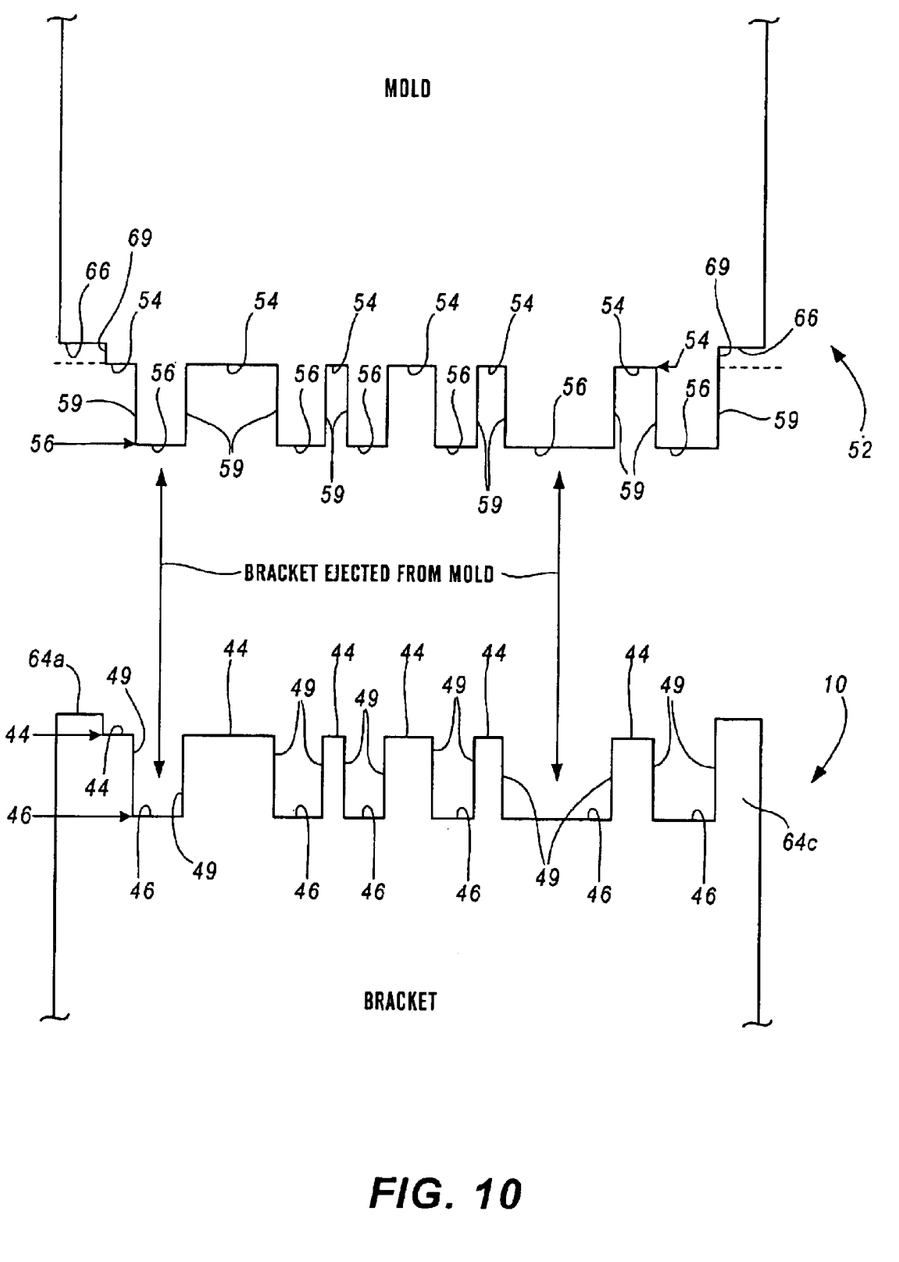
FIG. 10 is a cross-sectional view of a bracket and a mold used to form the bracket.

In yet a separate aspect of the invention, the surface finish of the base is manufactured to provided a finish having textural characteristics suited for use with characters 48. More particularly, the present invention includes a method of making the bracket 10 and its base 32 that is specifically suited for a bracket 10 with a base 32 having a continuous pattern of characters 48. In a preferred embodiment, a one-piece molded metal injected bracket 10 is manufactured from a mold 52. As known to those skilled in the art, the mold 52 is produced by electrical discharge machining using shaped electrodes to form the mold 52 itself. More specifically, the shaped electrodes are formed to correspond to the desired shape of at least a portion of one of the exterior surfaces of the bracket 10, such as the exterior surface that forms base 32. The shaped electrodes are then charged and placed in contact with a metal shape that will form a portion of mold 52 for production of the actual brackets 10. More specifically, the charged electrode "burns" the desired bracket pattern into the metal shape, thus forming a portion of mold 52. The mold is typically formed from a top and a bottom portion that is then assembled to form a hollow space that defines the bracket 10. The mold 52 is then used to manufacture a bracket 10 by injecting the mold 52 with the bracket material, such as molten stainless steel, via an injection channel that passes through mold 52 to the interior hollow region defining the bracket form. The molten stainless steel is allowed to cool and harden, and then the mold 52 is separated and molded bracket 10 is subsequently ejected from the mold 52.

In order to adequately bond the bracket 10 having a continuous pattern of characters 48 to the tooth surface using an adhesive, the surfaces of the base 32 that are parallel to the tooth's surface are preferably relatively rough. However, if the surfaces of mold 52 corresponding to the base 32 of bracket 10 are too rough, the actual bracket 10 cannot be ejected from the mold 52 during the bracket manufacturing process. Thus, in this separate aspect of the invention, the mold 52 is preferably manufactured and processed to have appropriate surficial roughness textures along its corresponding base surfaces.

Referring now to FIG. 10, the mold 52 has a base that includes mold recessed surface 54 and mold projected surface 56, which correspond to the projected surface 44 and the recessed surface 46 of bracket 10, respectively. Preferably, mold recessed surface 54 and mold projected surface 56 have a surface finish of approximately a maximum of 110.8 micro-inches. In contrast, preferably the mold character walls 59 of mold 52 that form the generally sloped or perpendicular surfaces between characters 48 and intermediate spaces 50 of bracket 10 are polished. More specifically, the mold character walls 59 of mold 52 are preferably hand polished to a relatively smooth and polished finish, preferably using a ruby stone, although other means may be employed. Upon manufacture of a bracket 10 from mold 52, the hand polished character walls 59 of the mold 52 allow the actual bracket 10 to be ejected from the mold 52 because the character walls 49 of bracket 10 are formed to have a smooth and polished finish that corresponds to the polished mold character walls 59 from which they were formed. Thus, the bracket 10 may be ejected from mold 52 without sticking to the mold 52 and thereby preventing ejection from occurring, or bending or otherwise causing detrimental structural damage to the bracket 10 during the ejection process. An ejector pin (not shown) may be used to aid the ejection process, wherein the ejection pin forceably separates the bracket 10 from the mold 52 by pushing base 32 away from mold 52.

Where a perimeter rail is used, preferably the bonding surface 66 of the perimeter rail of mold 52 that is parallel to the tooth's surface is surficially textured to improve bonding between the bracket 10 and the surface of the tooth. More particularly, the bonding surfaces 66 of the perimeter rail of the mold 52 preferably have a surface finish of approximately a maximum of 110.8 micro-inches. In contrast, preferably the perimeter rail walls 69 of the discontinuous perimeter rail of mold 52 are polished to a smooth finish to prevent an injected bracket 10 from sticking to the mold 52 during the ejection process, thereby preventing ejection or otherwise causing detrimental structural damage to the bracket 10 during the ejection process.

Figure 11:
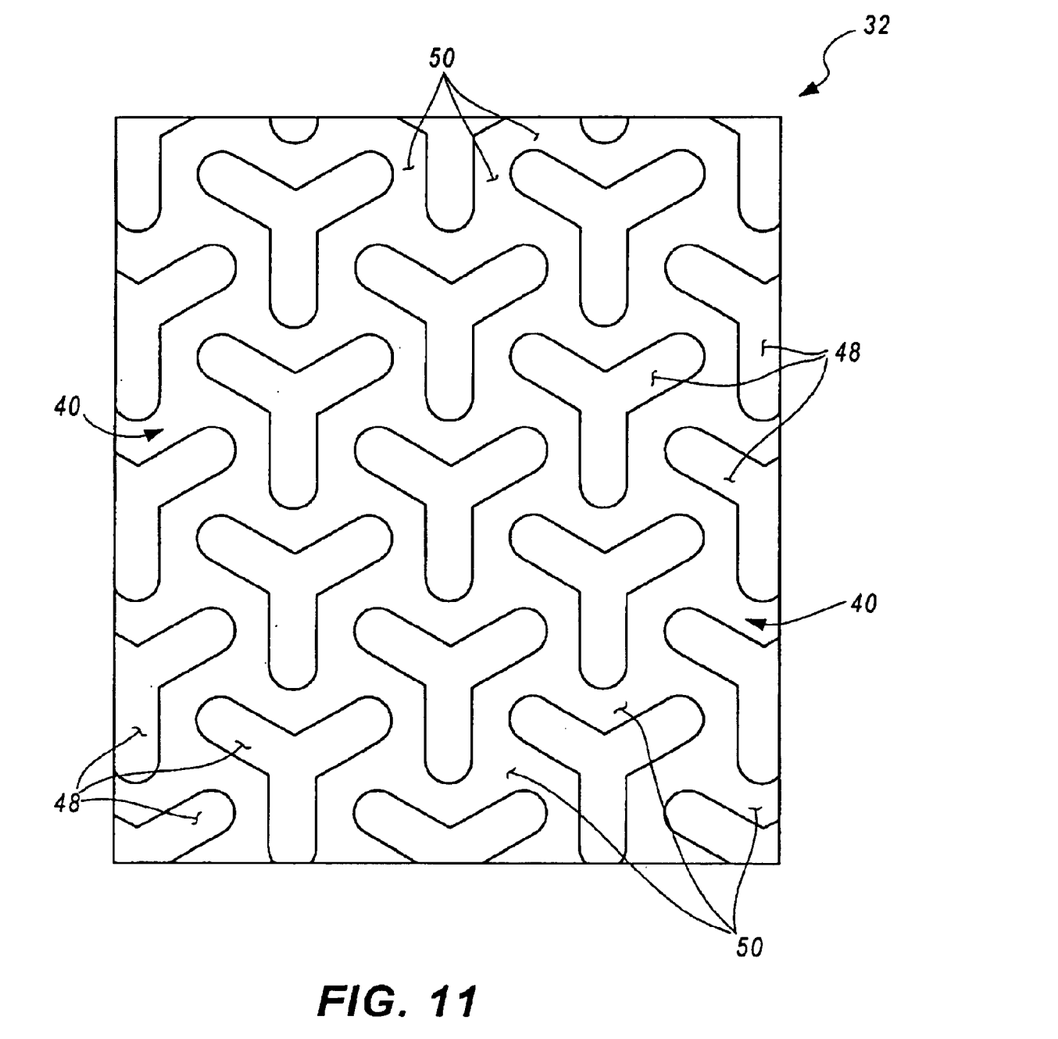
FIG. 11 is a separate embodiment of the present invention.

Referring now to FIG. 11, an alternate aspect of the invention is shown. FIG. 11 presents a pattern of characters 48, wherein the characters are a three-pronged shape resembling the letter "Y". As in the previously described embodiments, intermediate space 50 surrounds the characters 48 within the interior region 40 of the base 32. Accordingly, the present invention contemplates the use of patterns of characters 48 wherein the character is a seemingly arbitrary shape, and one in which the base 32 possesses a projected surface 44 and a recessed surface 46. Brackets 10 that included patterns of characters 48 of shapes may further include discontinuous perimeter rail structures as described above.

In summary, the present invention is unique in that it provides a device for providing a continuous pattern of characters on the base of an orthodontic bracket. Characters are preferably formed by creating a recessed pattern of characters in the base, with the area between the characters raised, such that the area between the characters is closer to the tooth surface when the bracket is applied to the surface of a patient's tooth using an adhesive. Alternatively, the characters may be raised and projecting relative to the area between the characters, such that the characters are closer to the tooth surface when the bracket is attached to the surface of a patient's tooth.

In a separate aspect of the invention, a discontinuous perimeter rail may be used around the character pattern of the base. Preferably, the discontinuous perimeter rail includes four separate corner sections and two additional separate straight sections along the gingival and occlusal edges of the base. When used, the discontinuous perimeter rail projects beyond the patterned surface of the base, such that the discontinuous perimeter rail is closest to the tooth surface when the bracket is attached to a patient's tooth. The discontinuous perimeter rail increases the bonding strength of the bracket to the tooth's surface.

The substantially continuous pattern of characters and intermediate space formed on the base of an orthodontic bracket provides a texturing pattern (e.g., an ordered array of projecting features) for bonding the bracket to a patient's tooth using an adhesive, while at the same time providing a means of presenting information about the bracket on its base surface by advantageously utilizing characters that represent pertinent information, such as the name of the bracket manufacturer, the intended location for the bracket placement, or a graphics symbol or logo.

The invention presented herein has been described with respect to preferred embodiments; however, other changes and modifications to the invention may be made which are still contemplated within the spirit and scope of the invention.

What is claimed is:

1. An orthodontic bracket comprising:
   a body; and
   a base connected to said body, said base including an exterior surface, said exterior surface including a substantially continuous pattern of characters and intermediate space, wherein said characters and said intermediate space are separated by a character wall, wherein said character wall has a polished surface.

2. The bracket as claimed in claim 1, wherein said body and said base are one piece.

3. The bracket as claimed in claim 2, wherein said bracket is made of a material selected from the group consisting of plastic, metal, and ceramic.

4. The bracket as claimed in claim 2, wherein said bracket is made of stainless steel.

5. The bracket as claimed in claim 1, wherein said intermediate space is in contact with a tooth when said bracket is attached to a patient's tooth.

6. The bracket as claimed in claim 1, wherein said characters are in contact with a tooth when said bracket is attached to a patient's tooth.

7. The bracket as claimed in claim 1, wherein said characters have a line width of between about 0.008 and 0.010 inches wide.

8. The bracket as claimed in claim 1, wherein said characters reside in a recessed surface of said base.

9. The bracket as claimed in claim 8, wherein said recessed surface comprises between about 50% to 60% of said exterior surface of said base.

10. The bracket as claimed in claim 8, wherein said recessed surface comprises about 55% of said exterior surface.

11. The bracket as claimed in claim 1, wherein said intermediate space forms a projected surface of said base.

12. The bracket as claimed in claim 11, wherein said projected surface comprises between about 40% to 50% of said exterior surface of said base.

13. The bracket as claimed in claim 11, wherein said projected surface comprises about 45% of said exterior surface.

14. The bracket as claimed in claim 1, wherein said intermediate space forms a projected surface of said base, said characters form a recessed surface of said base, and wherein said recessed surface is recessed between about 0.009 and 0.011 inches relative to said projected surface.

15. The bracket as claimed in claim 1, wherein said intermediate space forms a projected surface of said base, said characters form a recessed surface of said base, and wherein said recessed surface is recessed about 0.010 inches relative to said projected surface.

16. The bracket as claimed in claim 1, wherein said intermediate surface has a surface finish of less than about 110.8 micro-inches.

17. The bracket as claimed in claim 1, wherein said characters have a surface finish of less than about 110.8 micro-inches.

18. The bracket as claimed in claim 1, wherein said characters are alpha/numeric and convey to a user of said bracket information selected from the group consisting of: model number, manufacturer, date of manufacture, lot number, distributor, placement data, and bracket data.

19. The bracket as claimed in claim 1, further comprising a discontinuous perimeter rail.

20. The bracket as claimed in claim 19, wherein said discontinuous perimeter rail comprises a distal/gingival corner, a gingival/mesial corner, a mesial/occlusal corner, and an occlusal/distal corner, wherein said distal/gingival corner, said gingival/mesial corner, said mesial/occlusal corner, and said occlusal/distal corner are separated from one another by a distance.

21. The bracket as claimed in claim 20, further comprising a gingival straight segment between said distal/gingival corner and said gingival/mesial corner.

22. The bracket as claimed in claim 20, further comprising an occlusal straight segment between said mesial/occlusal corner and said occlusal/distal corner.

23. The bracket as claimed in claim 20, wherein said bracket does not have a distal straight segment between said distal/gingival corner and said occlusal/distal corner.

24. The bracket as claimed in claim 20, wherein said bracket does not have a mesial straight segment between said gingival/mesial corner and said mesial/occlusal corner.

25. The bracket as claimed in claim 19, wherein said discontinuous perimeter rail is in contact with a tooth's surface when said bracket is attached to a patient's tooth.

26. The bracket as claimed in claim 19, wherein said discontinuous perimeter rail is between about 0.008 and 0.011 inches wide.

27. The bracket as claimed in claim 19, wherein said discontinuous perimeter rail has a surface finish of less than about 110.8 micro-inches.

28. The bracket as claimed in claim 19, wherein said intermediate space forms a projected surface of said base, said characters form a recessed surface of said base, wherein said recessed surface is recessed between about 0.009 and 0.011 inches relative to said projected surface, and said discontinuous perimeter rail projects between about 0.002 and 0.004 inches beyond said projected surface.

29. An orthodontic bracket comprising:
   a body;
   a base connected to said body, wherein said base is molded together with said body such that said body and said base are one-piece, said base having a continuous pattern of characters and intermediate space, wherein said characters are recessed relative to said intermediate space, wherein said characters and said intermediate space are separated by a character wall, and wherein said character wall has a polished surface.

30. The bracket as claimed in claim 29, wherein said bracket is made of a material selected from the group consisting of plastic, metal, and ceramic.

31. The bracket as claimed in claim 29, wherein said bracket is made of stainless steel.

32. The bracket as claimed in claim 29, further comprising a discontinuous perimeter rail.

33. The bracket as claimed in claim 32, wherein said discontinuous perimeter rail comprises a distal/gingival corner, a gingival/mesial corner, a mesial/occlusal corner, and an occlusal/distal corner, wherein said distal/gingival corner, said gingival/mesial corner, said mesial/occlusal corner, and said occlusal/distal corner are separated from one another by a distance.

34. The bracket as claimed in claim 33, further comprising a gingival straight segment between said distal/gingival corner and said gingival/mesial corner.

35. The bracket as claimed in claim 33, further comprising an occlusal straight segment between said mesial/occlusal corner and said occlusal/distal corner.

36. An orthodontic bracket comprising:
    a body; and
    a base connected to said body, said base including a discontinuous perimeter rail having a perimeter length and at least one cavity along said length, wherein said discontinuous perimeter rail comprises a distal/gingival corner, a gingival/mesial corner, a mesial/occlusal corner, and an occlusal/distal corner, and wherein said distal/gingival corner, said gingival/mesial corner, said mesial/occlusal corner, and said occlusal/distal corner are separated from one another by at least one cavity.

37. The bracket as claimed in claim 36, wherein said discontinuous perimeter rail includes at least one gingival straight segment.

38. The bracket as claimed in claim 36, wherein said discontinuous perimeter rail includes at least one occlusal straight segment.

39. The bracket as claimed in claim 36, further comprising a gingival straight segment, wherein said gingival straight segment is separated from said distal/gingival corner and said gingival/mesial corner by a distance.

40. The bracket as claimed in claim 39, wherein said discontinuous perimeter rail includes a width, and said distance is about the size of said width.

41. The bracket as claimed in claim 39, wherein said distance is between about 0.008 and 0.011 inches.

42. The bracket as claimed in claim 39, wherein said distance is about 0.0085 inches.

43. The bracket as claimed in claim 36, further comprising an occlusal straight segment, wherein said occlusal straight segment is separated from said mesial/occlusal corner and said occlusal/distal corner by a distance.

44. The bracket as claimed in claim 43, wherein said discontinuous perimeter rail includes a width, and said distance is about the size of said width.

45. The bracket as claimed in claim 43, wherein said distance is between about 0.008 and 0.011 inches.

46. The bracket as claimed in claim 43, wherein said distance is about 0.0085 inches.

47. The bracket as claimed in claim 36, wherein said base includes an exterior surface that includes said discontinuous perimeter rail.

48. The bracket as claimed in claim 47, wherein said base further comprises a projected surface.

49. The bracket as claimed in claim 48, wherein said projected surface comprises intermediate space.

50. The bracket as claimed in claim 48, wherein said projected surface comprises between about 35% to 40% of said exterior surface of said base.

51. The bracket as claimed in claim 47, wherein said discontinuous perimeter rail comprises between about 12% to 16% of said exterior surface of said base.

52. The bracket as claimed in claim 47, wherein said base further comprises a recessed surface.

53. The bracket as claimed in claim 52, wherein said recessed surface comprises characters.

54. The bracket as claimed in claim 52, wherein said recessed surface comprises between about 45% to 50% of said exterior surface of said base.

55. The bracket as claimed in claim 52, wherein said recessed surface comprises about 48% of said exterior surface of said base.

56. The bracket as claimed in claim 48, wherein said projected surface comprises about 38% of said exterior surface of said base.

57. A method of improving the bonding strength of an orthodontic bracket, comprising:
    providing a bracket having a base comprising an interior base area partially surrounded by a discontinuous perimeter rail having at least one cavity along its length, wherein said discontinuous perimeter rail comprises a distal/gingival corner, a gingival/mesial corner, a mesial/occlusal corner, and an occlusal/distal corner, wherein said distal/gingival corner, said gingival/mesial corner, said mesial/occlusal corner, and said occlusal/distal corner are separated from one another by a distance;
    applying an adhesive at least within the interior base area of the bracket; and
    placing the bracket in contact with a patient's tooth, wherein the cavity within the discontinuous perimeter rail allows excess adhesive to escape from the interior base area during said placing step.

58. The method as claimed in claim 57, wherein the discontinuous perimeter rail includes at least one straight segment.

59. The method as claimed in claim 57, wherein the interior base area includes a projected surface and a recessed surface.

60. The method as claimed in claim 59, wherein at least one of either the projected surface or the recessed surface comprises characters.

61. The method as claimed in claim 59, wherein the discontinuous perimeter rail is disposed between about 0.002 and 0.004 inches beyond the projected surface.

62. The method as claimed in claim 59, wherein the discontinuous perimeter rail is disposed about 0.003 inches beyond the projected surface.

63. A method of making injection molded orthodontic brackets comprising the following steps:
    manufacturing a mold using an electrical discharge machining process, wherein the mold has a portion for forming a base including a pattern having a series of characters and an intermediate space between and around the characters, and wherein the characters and the intermediate space occupy different surfaces, the surfaces separated by character walls;
    smoothing the character walls of the mold to a polished finish;
    injecting the mold with a material to form an orthodontic bracket.

64. The method as claimed in claim 63, wherein said smoothing step is performed using a ruby stone.

65. The method as claimed in claim 63, wherein said injecting step is performed by injecting a material selected from the group consisting of metal, plastic, and ceramic.

66. The method as claimed in claim 63, wherein said injecting step is performed by injecting molten stainless steel into the mold.

67. The method as claimed in claim 63, wherein said smoothing step is performed by hand manipulation of a ruby stone polishing tool.

68. The method as claimed in claim 63, wherein the mold is further characterized by having a structure for forming a discontinuous perimeter rail at the base of the bracket.

69. The method as claimed in claim 68, further comprising the step of smoothing a perimeter rail wall of the perimeter rail prior to said injecting step.

70. The method as claimed in claim 69, wherein said step of smoothing the perimeter rail wall is performed using a ruby stone.

71. An orthodontic bracket comprising:
a body;
a base connected to said body, wherein said base is molded together with said body such that said body and said base are one-piece, said base including an exterior surface comprising a recessed surface, a projected surface, and a discontinuous perimeter rail, wherein said discontinuous perimeter rail comprises a distal/gingival corner, a gingival/mesial corner, a mesial/occlusal corner, and an occlusal/distal corner, wherein said distal/gingival corner, said gingival/mesial corner, said mesial/occlusal corner, and said occlusal/distal corner are separated from one another by a distance.

72. The bracket as claimed in claim 71, wherein said bracket is made of a material selected from the group consisting of plastic, metal, and ceramic.

73. The bracket as claimed in claim 71, wherein said bracket is made of stainless steel.

74. The bracket as claimed in claim 71, further comprising a gingival straight segment between said distal/gingival corner and said gingival/mesial corner.

75. The bracket as claimed in claim 71, further comprising an occlusal straight segment between said mesial/occlusal corner and said occlusal/distal corner.

76. The bracket as claimed in claim 71, wherein said bracket does not have a distal straight segment between said distal/gingival corner and said occlusal/distal corner.

77. The bracket as claimed in claim 71, wherein said bracket does not have a mesial straight segment between said gingival/mesial corner and said mesial/occlusal corner.

78. The bracket as claimed in claim 71, wherein said recessed surface comprises between about 45% to 50% of said exterior surface.

79. The bracket as claimed in claim 71, wherein said projected surface comprises between about 35% to 40% of said exterior surface.

80. The bracket as claimed in claim 71, wherein said discontinuous perimeter rail comprises between about 12% to 16% of said exterior surface.

81. The bracket as claimed in claim 71, wherein said discontinuous perimeter rail is disposed between about 0.002 and 0.004 inches beyond said projected surface.

82. The bracket as claimed in claim 71, wherein said discontinuous perimeter rail is disposed about 0.003 inches beyond said projected surface.

83. The bracket as claimed in claim 71, wherein said projected surface comprises intermediate space.

84. The bracket as claimed in claim 71, wherein said recessed surface comprises characters.

85. An orthodontic bracket comprising:
a body;
a base connected to said body wherein said body and said base are one piece, said base including an exterior surface having a substantially continuous pattern of characters and intermediate space, said characters having:
a line width of between about 0.008 and 0.010 inches wide; and
residing in a recessed surface of said base and comprising between about 45% to 50% of said exterior surface;
said intermediate space:
forming a projected surface of said base that comprises between about 35% to 40% of said exterior surface;
wherein said recessed surface is recessed between about 0.009 and 0.011 inches relative to said projected surface, wherein said characters and said intermediate surface have a surface finish of less than about 110.8 micro-inches and are separated by a character wall having a polished surface;
a discontinuous perimeter rail at the boundary of said exterior surface and comprising between about 12% to 16% of said exterior surface, said discontinuous perimeter rail having a surface finish of less than about 110.8 micro-inches, a width between about 0.008 and 0.011 inches, and projecting between about 0.002 and 0.004 inches beyond said projected surface, said discontinuous perimeter rail further comprising:
a distal/gingival corner;
a gingival/mesial corner;
a mesial/occlusal corner; and
an occlusal/distal corner;
wherein said distal/gingival corner, said gingival/mesial corner, said mesial/occlusal corner, and said occlusal/distal corner are separated from one another by a distance, said discontinuous perimeter rail further comprising:
a gingival straight segment between said distal/gingival corner and said gingival/mesial corner; and
an occlusal straight segment between said mesial/occlusal corner and said occlusal/distal corner;
wherein said discontinuous perimeter rail does not have a distal straight segment between said distal/gingival corner and said occlusal/distal corner, and does not have a mesial straight segment between said gingival/mesial corner and said mesial/occlusal corner.

86. The bracket as claimed in claim 85, wherein said characters are alpha/numeric and convey to a user of said bracket information selected from the group consisting of: model number, manufacturer, date of manufacture, lot number, distributor, placement data, and bracket data.

87. The bracket as claimed in claim 85, wherein said discontinuous perimeter rail is in contact with a tooth's surface when said bracket is attached to a patient's tooth.

88. The bracket as claimed in claim 85, wherein said bracket is made of a material selected from the group consisting of plastic, metal, and ceramic.

89. The bracket as claimed in claim 85, wherein said bracket is made of stainless steel.

90. An orthodontic bracket comprising:
a body; and
a base connected to said body, said base including an exterior surface, said exterior surface including a substantially continuous pattern of characters and intermediate space, wherein said characters are alpha/numeric and convey to a user of said bracket information selected from the group consisting of: model number, manufacturer, date of manufacture, lot number, distributor, placement data, and bracket data.

91. An orthodontic bracket comprising:
a body; and
a base connected to said body, said base including an exterior surface, said exterior surface including a substantially continuous pattern of characters and intermediate space, said base further comprising a discontinuous perimeter rail wherein said discontinuous perimeter rail comprises a distal/gingival corner, a gingival/mesial corner, a mesial/occlusal corner, and an occlusal/distal corner, wherein said distal/gingival corner, said gingival/mesial corner, said mesial/occlusal corner, and said occlusal/distal corner are separated from one another by a distance.

* * * * *